United States Patent [19]
Noel et al.

[11] Patent Number: 5,558,832
[45] Date of Patent: Sep. 24, 1996

[54] APPARATUS FOR SORTING SUBSTRATE COMPONENTS ACCORDING TO SIZE AND METHOD OF SORTING SUBSTRATE COMPONENTS THEREWITH

[75] Inventors: John R. Noel, Cincinnati; Mark R. Richards, Middletown, both of Ohio

[73] Assignee: The Procter & Gamble Company, Cincinnati, Ohio

[21] Appl. No.: 519,475

[22] Filed: Aug. 25, 1995

[51] Int. Cl.⁶ .................... B27N 3/04; B27N 3/02
[52] U.S. Cl. .................... 264/510; 264/518; 264/113; 425/811; 425/83.1
[58] Field of Search .................... 264/518, 113, 264/121, 510; 425/81.1, 83.1

[56] References Cited

U.S. PATENT DOCUMENTS

| | | | |
|---|---|---|---|
| Re. 32,649 | 4/1988 | Brandt et al. | 604/368 |
| 3,707,244 | 12/1972 | Hull et al. | 221/13 |
| 3,941,684 | 3/1976 | Bradbury et al. | 209/3 |
| 4,284,496 | 8/1981 | Newton | 209/3.3 |
| 4,457,434 | 7/1984 | Brown et al. | 209/539 |
| 4,756,427 | 7/1988 | Gohde et al. | 209/3.1 |
| 4,927,582 | 5/1990 | Bryson | 264/113 |
| 4,929,342 | 5/1990 | Johnston | 209/12 |
| 5,429,788 | 7/1995 | Ribble et al. | 264/510 |
| 5,466,409 | 11/1995 | Partridge et al. | 264/165 |
| 5,494,622 | 2/1996 | Heath et al. | 264/40.1 |
| 5,498,115 | 3/1996 | Perneborn | 414/326 |

*Primary Examiner*—Mary Lynn Theisen
*Attorney, Agent, or Firm*—Larry L. Huston; E. Kelly Linman; Jacobus C. Rasser

[57] ABSTRACT

A forming station used to make a substrate. The forming station has a forming chamber which deposits particles and fibers from an air carrier onto a forming screen movable relative to the forming chamber. Inside the forming chamber is at least one baffle, which creates a velocity gradient and low pressure zone for the air carrier. Different sized components of the substrate have different momentums, and thus are differently affected by the velocity gradient and low pressure zone. This difference causes the different sized components to be sorted according to size. The sorted components are then distributed according to size within the substrate.

15 Claims, 3 Drawing Sheets

APPARATUS FOR SORTING SUBSTRATE COMPONENTS ACCORDING TO SIZE AND METHOD OF SORTING SUBSTRATE COMPONENTS THEREWITH

CROSS REFERENCE TO RELATED APPLICATIONS

This application claims the benefit of U.S. Application Ser. No. 08/353,650 filed Dec. 8, 1994, now U.S. Pat. No. 5,445,777, issued Aug. 29, 1995.

FIELD OF INVENTION

The present invention is related to a forming station for the components of a fibrous matrix, particularly to a forming station capable of sorting the components according to size, and more particularly to a forming station capable of depositing different sized components at different locations in the fibrous matrix.

BACKGROUND OF THE INVENTION

Disposable absorbent articles, such as sanitary napkins and diapers, often contain an absorbent substrate. As used herein a "substrate" refers to a fibrous matrix and, optionally, absorbent particulate materials. The fibers making up the fibrous matrix and/or the particles intermixed with the fibers are hereunder referred to as "substrate components."

The fibers may be synthetic, cellulosic, bicomponents or blends and strata thereof. The fibers may be used in tissue, nonwoven materials, etc.

The absorbent particles are commonly disposed or dispersed in the fibrous matrix by using a forming station. The absorbent particles are also well known in the art. Absorbent particles are commonly referred to as superabsorbents, absorbent gelling materials, supersorbers, osmotic absorbent materials, etc. Such absorbent particles are commonly used in disposable absorbent articles to absorb body fluids. Particularly well known and commercially successful absorbent particles can be made according to commonly assigned U.S. Pat. No. Re. 32,649 reissued to Brandt et al, which patent is incorporated herein by reference.

Conventional forming stations use a single air stream to transport and distribute blends of two or more materials which are different in characteristic or composition, such as, for example, absorbent particles and fibrous materials which make up a substrate or a blend of two different fibers. Conventional forming stations cannot produce substrates having multiple zones of substrate component concentrations in the Z-direction. Nor can a conventional forming station arrange substrate components according to fiber size.

Transporting the absorbent particles and fibrous materials to form absorbent bodies using separate air streams in an air laying forming station has been proposed, for example in U.S. Pat. No. 4,927,582, issued to Bryson. In Bryson, blower 48 propels absorbent particles 28 via one or more pipeline conduits 20 into forming chamber 10. Vacuum source 32 creates an air flow, indicated by arrows 36, which draws fibrous materials 14 against forming screen 30. Baffles 34 are attached to opposing side walls and are used to regulate the cross-directional distribution of absorbent particles across web 41. Conventional air laying forming stations simply cannot overcome the proclivity to provide a homogeneous blend of absorbent particles in a fibrous matrix, as opposed to zoned or variable concentrations.

However, a homogenous blend of substrate components is not necessarily, and not even usually, the most desired arrangement of the absorbent particles and fibers in order to optimize fluid handling properties. To the contrary, it may be important to have larger substrate components, particularly absorbent particles, on one side of the substrate so that in use they receive the first insult of fluids and do not cause undue gel blocking to occur. Additionally, a Z-direction pore size gradient in fibrous substrate components can assist in absorbing bodily fluids.

To the contrary, it may be desirable in, for example, a disposable diaper, to have the larger sized absorbent particles more highly concentrated on the side of the substrate near the wearer. This is because larger sized particles tend to absorb liquid more slowly than smaller sized particles. This arrangement of particles according to their size allows fluid to penetrate more deeply into the substrate before being absorbed by the absorbent particles, thus reducing the tendency for gell blocking to occur.

Additionally, it may be desirable to sort the fibrous materials, such as pure fibers, according to size. Frequently the fibrous materials form clumps, which may be undesirably randomly dispersed throughout the substrate. Furthermore, it may be desirable to arrange substrate components in a disposable absorbent article with the larger substrate components (such as particles or flakes) more concentrated in the center of the disposable absorbent article where fluid is received, and smaller substrate components more highly concentrated at the edges of the disposable absorbent article.

Accordingly, it is an object of this invention to provide a forming station which sorts and distributes absorbent particles and/or fibrous materials throughout a fibrous matrix according to the size of such substrate components. It is further an object of this invention to provide such a forming station capable of manufacturing a substrate of absorbent particles in a fibrous matrix of any desired width, so that economy of scale can be obtained. Finally, it is an object of this invention to provide such a forming station that can be readily adjusted so that modifications to the particle size and/or fibrous materials sorting operations are easily accomplished.

SUMMARY OF INVENTION

The invention comprises a forming station for dispersing substrate components, such as particles of different sizes in a matrix of fibers, to create a substrate of fibers and, optionally, particles. The forming station has a machine direction, a longitudinal centerline parallel the machine direction, a cross machine direction perpendicular to the machine direction, and a Z-direction mutually orthogonal to the machine and cross machine directions. The forming station further comprises a forming chamber and a forming screen movable in the machine direction relative to the forming chamber. The forming screen receives substrate components from the forming chamber. There is at least one material distributor for distributing substrate components, typically the fibers, on the forming screen. There is also at least one baffle disposed in the forming chamber. The baffle creates a lateral flow of substrate components. The baffle has a differential pressure thereacross thereby creating a low pressure zone and hence, a velocity gradient. The velocity gradient causes substrate components of different sizes to be disposed in different positions on the forming screen due to having different velocity components parallel to the plane of the forming screen. A vacuum may be applied below and across the forming screen to cause the differential pressure.

In one embodiment, the baffle may be disposed adjacent a front wall of the forming chamber or a back wall of the forming chamber to create a monotonic distribution of the particles according to their size. In another embodiment, the baffle may be disposed along one or more side walls of the forming chamber, so that particles and/or fibrous materials are disposed in the cross machine direction according to particle size.

DETAILED DESCRIPTION OF THE INVENTION

Figure 1:
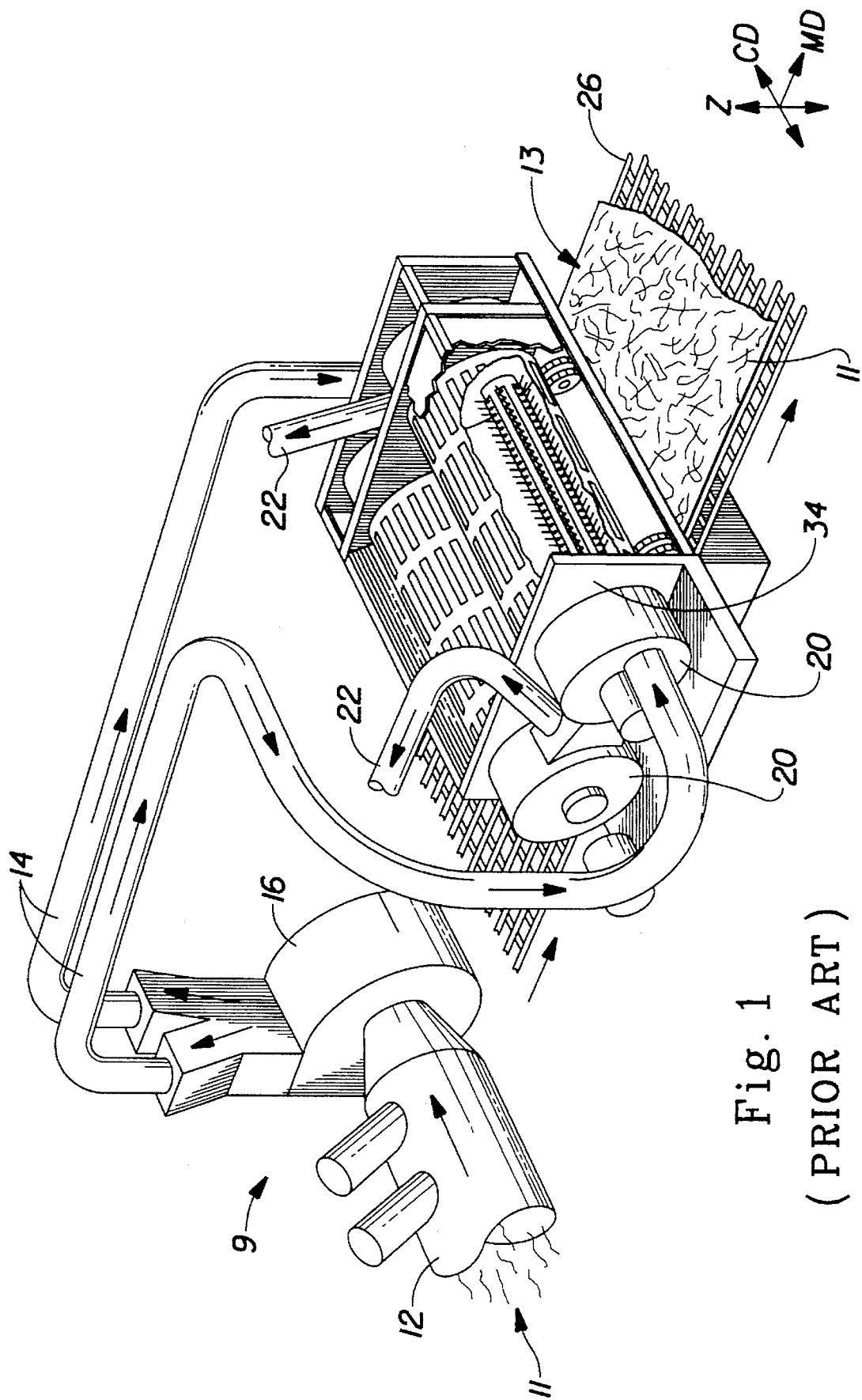
FIG. 1 is a perspective view of said forming station according to the prior art.

FIG. 1 illustrates a forming station 9 according to the prior art. Fibers 11 are provided at plenum 12. The fibers 11 are divided at the plenum 12 into two input tubes 14 extending from blower 16. The fibers 11 travel through the input tubes 14 into the cylindrical material distributors 20. Although two material distributors 20 are illustrated, any embodiment having at least one material distributor 20 with air flow therethrough is suitable. To promote even distribution of the fibers 11, the material distributors 20 are interconnected by a cross-over tube 22. The fibers 11, and/or particles 10 if present, may travel through the two material distributors 20, and are deposited by gravity, and preferably vacuum, on the forming screen 26 therebelow. The forming screen 26 moves relative to the material distributors 20 in a machine direction. For clarity, the vacuum is preferably provided below and across the forming screen 26, to assist in deposition of the fibers 11 upon the forming screen 26.

Figure 2:
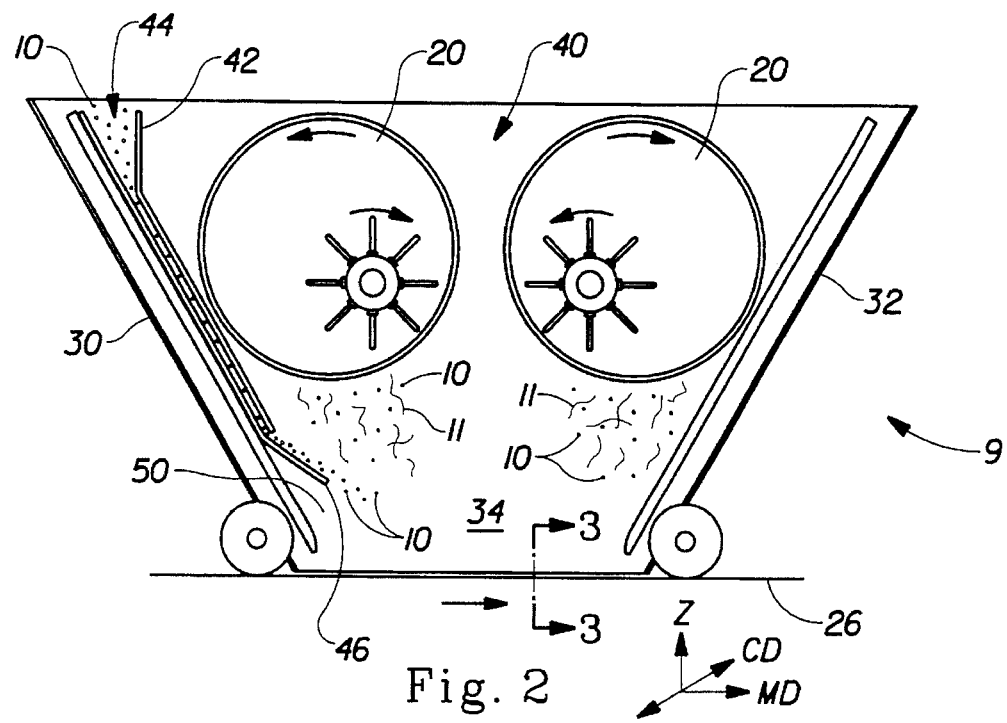
FIG. 2 is a side elevational view of a forming station according to the present invention, the drive motor and the vacuum source underneath the moving screen having been omitted for clarity.

FIG. 2 illustrates one forming station 9 according to the present invention which is especially useful for sorting particles 10 according to size. The forming station 9 can accommodate variable widths in the cross machine direction. The forming station 9 also has front and back walls 30, 32 and side walls 34 connecting the front and back walls. Collectively, the front back and side walls 30, 32, 34 are joined to provide a forming chamber 40. Of course, forming chambers 40 of other shapes are feasible as well.

Inside the forming chamber 40 is a baffle 42. The baffle 42 directs the absorbent particles 10 into the forming chamber 40, underneath the material distributors 20 and onto the forming screen 26. Substrate components, typically absorbent particles 10, are input at the top 44 of the baffle 42, and then fed by gravity and vacuum to the forming screen 26. Optionally, the absorbent particles 10 may be input through the material distributors 20.

Figure 4:
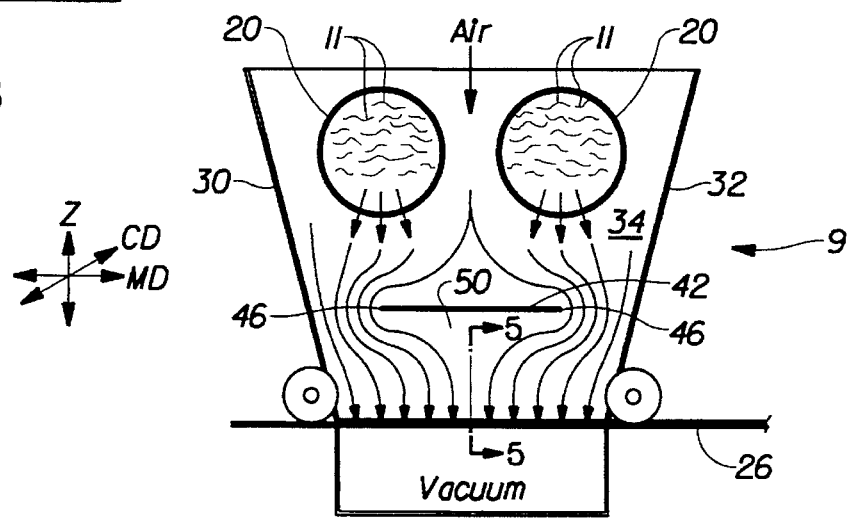
FIG. 4 is a simplified vertical elevation view of a forming station having a central baffle.
Figure 6A:
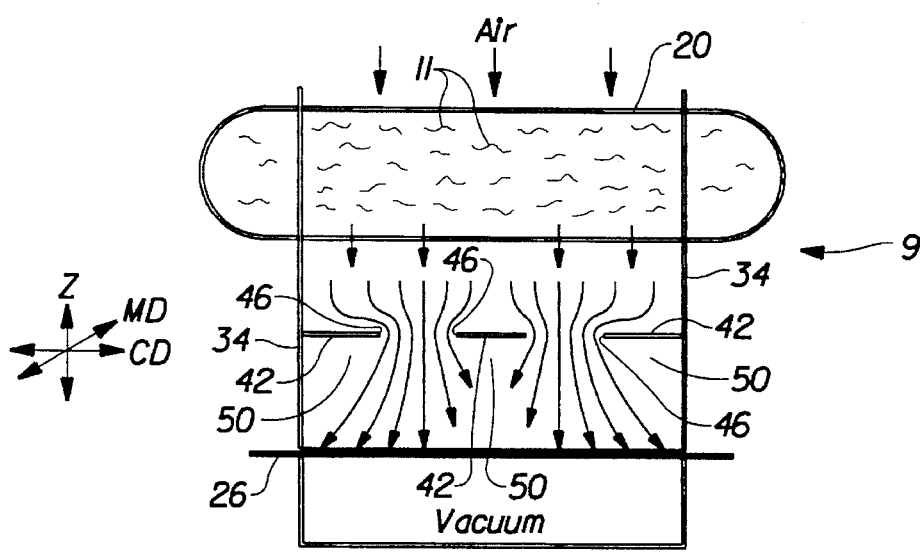
FIG. 6A is a simplified side elevation view of a forming station which produces a particle size gradient in the cross machine direction.

In one embodiment according to the present invention, it may be desirable to sort only the fibrous materials 10 according to size. This may be accomplished by interposing the baffle 42 between the material distributors 20 and the movable forming screen 26 as illustrated in FIGS. 4 and 6A.

This arrangement provides the benefits noted above that fluid handling properties may be optimized by proper and predetermined placement of the substrate components 10, 11 according to size. Of course, the forming station 9 may be used to sort fibrous materials 10 according to size when absorbent particles 10 are also present in the forming chamber 40.

The baffle 42 can be juxtaposed with or placed adjacent the front wall 30 as illustrated in FIG. 2. Alternatively, one skilled in the art will recognize the baffle 42 can be juxtaposed with or placed adjacent the back wall 32. Alternatively, two baffles 42 may be provided, one adjacent the front wall 30 and one adjacent the back wall 32. The baffle 42 may either be arcuately shaped, or have a plurality of straight sections joined at angles relative to one another as shown. Suitable baffles 42 may be made according to commonly assigned U.S. Pat. 5,445,777, issue date Aug. 29, 1995, which patent is incorporated herein by reference.

The baffle 42 creates a low pressure zone 50 behind and underneath the baffle 42. The low pressure zone 50 causes a velocity gradient to occur in the air currents carrying the substrate components, such as the absorbent particles 10, within forming chamber 40. Larger sized substrate components 10 have greater mass, and hence greater momentum Therefore, the larger substrate components 10 are less affected by the air flow than smaller sized absorbent particles 10, 11. This effect generally causes smaller sized substrate components 10, 11 to be deposited on the forming screen 26 at a position beneath and near the baffle 42.

Figure 3:
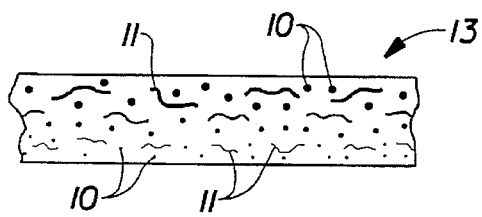
FIG. 3 is a fragmentary cross-sectional view of a substrate made on the forming station of FIG. 2.

Smaller sized substrate components 10, 11 are drawn by the higher velocity air into the low pressure zone 50. This draw causes the smaller sized substrate components 10, 11 to be sorted from the larger sized substrate components 10, 11 and to be distributed underneath the low pressure zone 50 created by the baffle 42. As illustrated by FIG. 3, such a velocity gradient causes the forming station 9 to deposit smaller size substrate components 10, 11 on the bottom of the substrate 13 and larger sized substrate components 10, 11 on the top of the substrate 13.

The distal end 46 of the baffle 42 may be adjusted to optimize the sorting and distribution of the absorbent particles 10. For example, the distal end 46 of the baffle 42 may be oriented more horizontal, i.e., more parallel to the machine direction and cross machine direction axes. This orientation has the effect of increasing the separation of different substrate components 10, 11. As used herein, "separation" refers to the amount of Z-direction distribution of the fibers 11 from the particles 10 in the substrate 13.

Alternatively, the distal end 46 of the baffle 42 may be lengthened or shortened. As the distal end 46 of the baffle 42 is lengthened or shortened, the particles 10 will be moved up or down in the substrate 13, respectively. As the elevation of the distal end 46 of the baffle 42 above the forming screen 26 increases, greater separation of the particles 10 in the substrate 13 occurs.

It will be apparent to one skilled in the art the illustrated arrangement can be reversed by juxtaposing the baffle 42 with the back wall 32 of the forming station 9. This arrangement would cause the smaller size substrate components 10, 11 to be disposed on the top of the substrate 13 rather than on the bottom of the substrate 13 as previously discussed.

Placing larger or smaller substrate components 10, 11 on either face of the substrate 13, provides a generally monotonic substrate component 10, 11 size distribution throughout the Z-direction of the substrate 13. A non-monotonic can be accomplished by the forming station 9 illustrated in FIG. 4.

Figure 5:
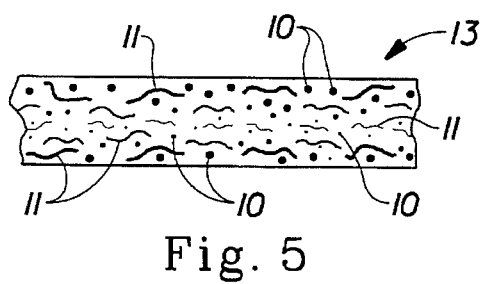
FIG. 5 is a fragmentary vertical sectional view of the substrate made on the forming station of FIG. 4.

In the forming station 9 of FIG. 4, the baffle 42 is placed below and between the two material distributors 20. The baffle 42 may be generally centered between the material distributors 20. This arrangement causes the low pressure zone 50 to occur in the center of the forming chamber 50, relative to the machine direction, producing the substrate 13 of FIG. 5.

Of course, consistent with the embodiment discussed above, the low pressure zone 50 occurs in the width direction across essentially the entire cross machine direction of the forming chamber 50. Using this arrangement, the smaller size substrate components 10, 11 are drawn into the low pressure zone 50 and intermediate two high pressure zones. This arrangement causes larger sized substrate components 10, 11 to be disposed in the outer sections of the absorbent substrate 13, whereas smaller sized substrate components 10, 11 are disposed nearer the center of the substrate 13. This arrangement reduces dusting of the substrate components 10, 11, especially particles 10, from the substrate 13, because the smaller sized substrate components 10, 11 are trapped in the center of the substrate 13.

Figure 6B:
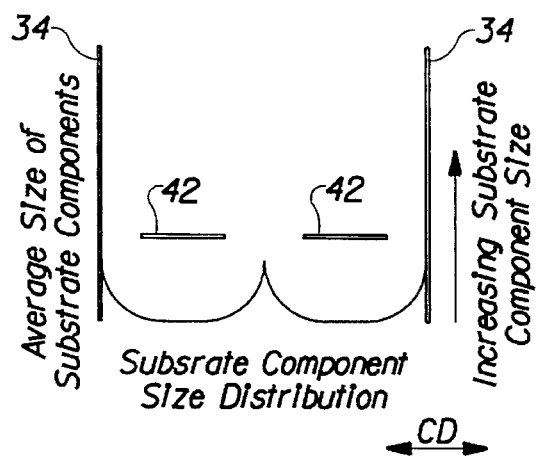
FIG. 6B illustrates a schematic representation of a two baffle system creating two machine direction oriented stripes in the substrate, and a relative substrate component size gradient distribution in the cross machine direction.
Figure 6C:
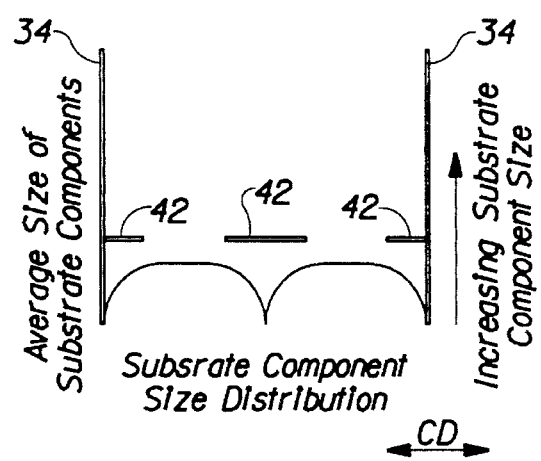
FIG. 6C illustrates a three baffle system wherein two of the baffles are disposed adjacent the side walls of the forming chamber, and creating two machine direction oriented stripes in the substrate, and a relative substrate component size gradient distribution in the cross machine direction.
Figure 7:
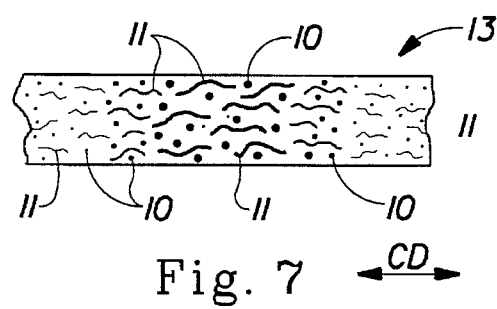
FIG. 7 is a fragmentary vertical sectional view of the substrate made on the forming station of FIG. 6A.

The central baffle 42 can be adjusted by making it longer in the machine direction. As the central baffle 42 becomes longer in the machine direction, the particle 10 separation increases. Smaller sized substrate components 10, 11 are moved upwardly in the substrate 13 relative to the larger sized substrate components 10, 11 as the cross machine direction centerline of the baffle 42 moves downstream in the machine direction. Referring to FIGS. 6A–6C, the forming station 9 may be provided with a plurality of baffles 42, causing low pressure zones 50 to be juxtaposed with both cross machine direction edges of the forming station 9. The plurality of low pressure zones 50 preferably occur along the entire machine direction length of the forming chamber 50. The plural baffle 42 arrangement of FIG. 6B causes the smaller sized substrate components 10, 11 to be drawn to the outside edges and center of the forming station 9. This arrangement results in a size distribution of substrate components 10, 11 to occur in the cross machine direction, rather than in the Z-direction, as discussed above. One repeating unit of the resulting substrate 13 is illustrated in FIG. 7.

More particularly, the forming station 9 may be provided with at least two baffles which are not disposed adjacent the side walls 34 of the forming chamber 40.

Referring to FIG. 6B, if a plurality of n baffles 42 are used, and the baffles 42 are not disposed along either side wall 34, a cross machine direction distribution of n machine direction oriented stripes of substrate components 10, 11 will result.

Referring to FIG. 6C, if a plurality of n baffles 42 are provided, with one baffle 42 being disposed along each side wall and at least one intermediate baffle 42, a plurality of n minus one machine direction oriented stripes will result.

It will be apparent to one skilled in the art that both the arrangement of the baffles 42, and the resulting machine direction stripes of substrate components 10, 11, will be symmetric about the longitudinal centerline of the forming station 9. Of course, each machine direction stripe is symmetric because laterally asymmetric designs are not preferred in the art. Of course, it will be recognized that while FIGS. 6B and 6C show pluralities of two and three baffles 42, respectively, the number of baffles 42 may be increased to any desired plurality.

The baffles 42 of the forming chamber 40 of FIG. 6A may be made longer or shorter as desired. As the width in the cross machine direction of the baffles 42 increase, greater separation of the substrate components 10, 11 occurs. Generally, the central baffle 42 should have a cross machine direction width about twice that of the outboard baffles 42, so that symmetry, is maintained in the resulting disposable absorbent article.

It will be apparent to one skilled in the art that the forming chamber 40 of FIG. 6B can prophetically be rotated 90 degrees about the Z-axis, such that the dual baffles 42 are juxtaposed with the front and back walls 30, 32. This arrangement would prophetically cause larger sized substrate components 10, 11 to be distributed in the center of the substrate 13, as taken in the Z-direction, as well as along the outer surfaces of the substrate 13. However, between the central and two outer regions of relatively larger size substrate components 10, 11 are interposed two regions of relatively smaller size substrate components 10, 11, resulting in a substrate 13 of five zones, three having relatively larger size substrate components 10, 11 and two having relatively smaller size substrate components 10, 11 alternating between relatively large and relatively small size substrate components 10, 11.

Instead of using absorbent particles 10 as the substrate component 11, any particulate material 11 desired for use with the present invention can be accommodated with the forming station 9 described and claimed herein. For example, the forming station 9 may be useful to distribute odor control particles 10, organic particles 10, or inorganic filler particles 10 used in papermaking. Additionally, opacifiers such as titanium dioxide or clay may be used for the particles 10. Of course, the baffles 42 must be adjusted for the density and the surface area to mass ratio of such particles 10.

What is claimed is:

1. A forming station for dispersing particles of different sizes in a matrix of fibers thereby creating a substrate of said fibers and said particles, said forming station having a machine direction, and a cross machine direction perpendicular to said machine direction, said forming station comprising:

a forming chamber;

a forming screen movable in the machine direction relative to said forming chamber, said forming screen receiving said particles and said fibers thereon;

at least one material distributor for distributing said fibers on said forming screen; and at least one baffle disposed in said forming chamber for distributing said particles on said forming screen, said baffle having a differential pressure thereacross, thereby creating a low pressure zone, whereby said low pressure zone creates a velocity gradient in the particles having a component parallel to the plane of the forming screen, whereby said baffle creates a monotonic distribution of said substrate components according to the size of said particles throughout the thickness of said substrate.

2. A forming station for dispersing particles of different sizes in a matrix of fibers thereby creating a substrate of said fibers and said particles, said forming station having a front wall and a back wall, said front wall and said back wall being connected by two side walls, said side walls being generally parallel a machine direction, a cross machine direction being perpendicular to said machine direction, said forming station comprising:

a forming chamber;

a forming screen movable in the machine direction relative to said forming chamber, said forming screen receiving said particles and said fibers thereon;

at least one material distributor for distributing said fibers on said forming screen;

at least one baffle disposed in said forming chamber having a differential pressure thereacross, thereby creating a component of velocity in said particles parallel to the plane of said forming screen, said baffle being disposed adjacent a front wall of said forming chamber or a back wall of said forming chamber, whereby said baffle creates a monotonic distribution of said substrate components according to the size of said particles throughout the thickness of said substrate.

3. A forming station for dispersing particles of different sizes in a matrix of fibers thereby creating a substrate of said fibers and said particles, said forming station having a front wall and a back wall, said front wall and said back wall being connected by two side walls, said side walls being generally parallel a machine direction, a longitudinal centerline parallel to said machine direction, a cross machine direction being perpendicular to said machine direction, said forming station comprising:

a forming chamber;

a forming screen movable in the machine direction relative to said forming chamber, said forming screen receiving said particles and said fibers thereon;

at least one material distributor for distributing said fibers on said forming screen; and a plurality of n baffles disposed in said forming chamber, each said baffle creating a differential pressure thereacross, and thereby creating a component of velocity in said particles parallel to the plane of said forming screen, whereby said n baffles create a velocity gradient in said forming chamber such that smaller sized particles are more affected by said velocity gradient, said particles being disposed in a plurality of an n minus one cross machine direction distributions, and no less than two cross machine direction distributions, said baffles being symmetrically disposed about said longitudinal centerline of said forming station.

4. A forming station according to claim 1 wherein said baffle creates a low pressure zone between said baffle and said movable forming screen.

5. A forming station according to claim 4 wherein said low pressure zone is below said at least one baffle.

6. A forming station according to claim 3 comprising at least three said baffles, one said baffle being juxtaposed with each of said side walls, and at least one said baffle being intermediate said baffles juxtaposed with said side walls.

7. A forming station according to claim 3 having one baffle disposed along each side wall of said forming chamber, and at least one intermediate baffle, wherein said plurality of n baffles creates n minus one cross machine direction distributions of said particles according to particle size.

8. A forming station for dispersing fibrous materials of different sizes in a substrate, said forming station having a machine direction, and a cross machine direction perpendicular to said machine direction, said forming station comprising:

a forming chamber;

a forming screen movable in the machine direction relative to said forming chamber, said forming screen receiving said fibrous materials thereon;

at least one material distributor for distributing said fibrous materials on said forming screen; and at least one baffle interposed between said at least one material distributor and said forming screen, said baffle having a differential pressure thereacross, thereby creating a low pressure zone, whereby said low pressure zone creates a velocity gradient in the fibrous materials having a component parallel to the plane of the forming screen, whereby said baffle creates a monotonic distribution of said substrate components according to the size of said particles throughout the thickness of said substrate.

9. A forming station according to claim 8 wherein said forming chamber has a front wall, a back wall, and at least one side wall, said at least one baffle being juxtaposed with one of said front wall or said back wall.

10. A forming station according to claim 9 comprising two baffles, one disposed along said front wall and said back wall.

11. A forming station according to claim 8 further comprising a means for distributing particles with said fibrous materials.

12. A method of sorting substrate components according to size and thereby creating a substrate, said method comprising the steps of:

providing a forming station, said forming station having a machine direction, a longitudinal centerline coincident said machine direction, and a cross machine direction perpendicular to said machine direction, said forming station further comprising a forming chamber, a forming screen movable in said machine direction relative to said forming chamber, said forming screen being adapted to receive components of said substrate thereon, at least one material distributor for distributing substrate components on said forming screen, and at least one baffle disposed in said forming chamber for distributing substrate components on said forming screen;

causing a differential pressure across said at least one baffle, said differential pressure creating a low pressure zone intermediate said baffle and said forming screen; and providing substrate components in said forming chamber, whereby said differential pressure and gravity causes said substrate components to be deposited on said forming screen, said baffle creating a velocity component parallel to said forming screen in said substrate components, and a velocity gradient in said substrate components having said parallel velocity component, whereby substrate components of different sizes are monotonically distributed throughout the thickness of said substrate.

13. A method according to claim 12 wherein said step of providing substrate components comprises the step of providing fibers in said material distributor.

14. A method according to claim 13 wherein said baffle has a predetermined elevation and said step of providing substrate components further comprises providing absorbent particles at a position above the elevation of said baffle.

15. A method according to claim 12 wherein said forming chamber comprises a front wall, a back wall, and two side walls, and said step of providing said at least one baffle comprises providing said baffle adjacent a front wall or a side wall.

* * * * *